(12) United States Patent
Davis et al.

(10) Patent No.: US 11,298,282 B2
(45) Date of Patent: Apr. 12, 2022

(54) INFLATABLE SUPPORT

(71) Applicant: D.T. Davis Enterprises, Ltd., Allentown, PA (US)

(72) Inventors: David T. Davis, Bethlehem, PA (US); Jason K. Werkheiser, Fogelsville, PA (US); John F. Englebert, III, Bethlehem, PA (US)

(73) Assignee: D.T. Davis Enterprises, Ltd., Allentown, PA (US)

( * ) Notice: Subject to any disclaimer, the term of this patent is extended or adjusted under 35 U.S.C. 154(b) by 138 days.

(21) Appl. No.: 16/061,956

(22) PCT Filed: Jan. 30, 2017

(86) PCT No.: PCT/US2017/015609
§ 371 (c)(1),
(2) Date: Jun. 13, 2018

(87) PCT Pub. No.: WO2017/132662
PCT Pub. Date: Aug. 3, 2017

(65) Prior Publication Data
US 2018/0369050 A1 Dec. 27, 2018

Related U.S. Application Data

(60) Provisional application No. 62/288,161, filed on Jan. 28, 2016.

(51) Int. Cl.
*A61G 13/12* (2006.01)
*A61B 5/00* (2006.01)
(Continued)

(52) U.S. Cl.
CPC .......... *A61G 13/1265* (2013.01); *A61B 5/055* (2013.01); *A61B 5/70* (2013.01);
(Continued)

(58) Field of Classification Search
CPC .. A61G 13/1265; A61G 13/12; A61G 7/1021; A61G 7/1013; A61G 2200/54;
(Continued)

(56) References Cited

U.S. PATENT DOCUMENTS 1,726,939 A * 9/1929 Anderson .............. A47C 7/021
267/117
2,612,645 A * 10/1952 Boland ................ A47C 20/048
5/644

(Continued)

FOREIGN PATENT DOCUMENTS

CA       2663508 C       3/2008

OTHER PUBLICATIONS

Office Action issued in connection with corresponding Canadian Patent Application No. 3,008,967, dated Apr. 4, 2019, 4 pages.

(Continued)

*Primary Examiner* — Robert G Santos
*Assistant Examiner* — Alison N Labarge
(74) *Attorney, Agent, or Firm* — Duane Morris LLP

(57) ABSTRACT

An inflatable patient support includes a top panel defining a first perimeter and a bottom panel defining a second perimeter. The second perimeter of the bottom panel is coupled to the first perimeter of the top panel. An internal wall is coupled between the top panel and the bottom panel to define a first chamber and a second chamber. The internal wall defines at least one passage therethrough that allows fluid communication between the first chamber and the second chamber. The first chamber and the second chamber are inflatable.

20 Claims, 9 Drawing Sheets

(51) Int. Cl.
  *A61B 6/04*     (2006.01)
  *A61G 7/10*     (2006.01)
  *A61B 5/055*    (2006.01)

(52) U.S. Cl.
  CPC ............ *A61B 5/702* (2013.01); *A61B 6/0485* (2013.01); *A61G 7/1021* (2013.01); *A61G 13/12* (2013.01); *A61G 2200/30* (2013.01); *A61G 2200/54* (2013.01)

(58) Field of Classification Search
  CPC ...... A61G 2200/30; A61B 5/702; A61B 5/70; A61B 5/0555; A61B 6/0485; A47C 27/081; A47C 27/087; A47C 27/10; A47C 27/08
  See application file for complete search history.

(56) References Cited

U.S. PATENT DOCUMENTS

| | | | | |
|---|---|---|---|---|
| 5,249,318 | A * | 10/1993 | Loadsman | A47C 27/10<br>5/423 |
| 5,287,577 | A * | 2/1994 | Bremer | A61B 6/04<br>5/601 |
| 2002/0125758 | A1 | 9/2002 | Duncan | |
| 2002/0166168 | A1 | 11/2002 | Weedling et al. | |
| 2005/0044634 | A1 * | 3/2005 | Wang | A47C 27/084<br>5/709 |
| 2005/0081299 | A1 | 4/2005 | Torres | |
| 2007/0006385 | A1 * | 1/2007 | Davis | A61G 7/1028<br>5/710 |
| 2007/0028380 | A1 * | 2/2007 | Russo | A61G 7/1021<br>5/81.1 R |
| 2008/0244830 | A1 | 10/2008 | Davis | |
| 2009/0144904 | A1 | 6/2009 | Moye | |
| 2011/0056502 | A1 | 3/2011 | Davis et al. | |
| 2011/0200177 | A1 | 8/2011 | Patton et al. | |
| 2012/0011658 | A1 * | 1/2012 | Weedling | A61G 7/065<br>5/710 |
| 2013/0025054 | A1 * | 1/2013 | Graw | A61B 6/0407<br>5/601 |
| 2013/0055504 | A1 * | 3/2013 | Peash | A61G 5/14<br>5/654 |
| 2014/0230154 | A1 * | 8/2014 | Palumbo | A47C 27/081<br>5/706 |
| 2015/0272771 | A1 * | 10/2015 | O'Brien | A61G 13/1265<br>128/847 |
| 2016/0186874 | A1 * | 6/2016 | Lin | A47C 27/081<br>137/232 |
| 2017/0332802 | A1 * | 11/2017 | Stern | A47C 7/021 |

OTHER PUBLICATIONS

International Search Report and Written Opinion for corresponding International patent application No. PCT/US2017/015609, dated Apr. 25, 2017.
European Patent Office, European Search Report for EP Application No. 17745079.8; Search Report dated Aug. 6, 2019.

* cited by examiner

INFLATABLE SUPPORT

CROSS-REFERENCE TO RELATED APPLICATION

This application is a U.S. national stage application under 35 U.S.C. § 371 of International Application No. PCT/US2017/015609; filed Jan. 30, 2017, which claims priority to U.S. Provisional Appl. Ser. No. 62/288,161, filed Jan. 28, 2016, the entireties of which are incorporated herein by reference.

BACKGROUND

Positioning patients for medical imaging and other procedures presents risks to both the patient and caregivers. Patients must be placed in a seated position and a device inserted to maintain the patient in the seated position. Often, this requires a caregiver to lift a patient, which can result in injury to the caregiver or require multiple caregivers. Moving and/or readjusting a patient who has certain injuries can also exacerbate such injuries.

The use of devices or supports to maintain a patient in a seated position can cause issues during imaging. Internal stringers, supports, or other structures can limit imaging and/or generate artifacts in images of patients. Such limitations and artifacts can result in false positive/negative results during medical imaging resulting in misdiagnosis and/or improper treatment.

SUMMARY

In various embodiments, an inflatable patient support is disclosed. The inflatable patient support includes a top panel defining a first perimeter and a bottom panel defining a second perimeter. The second perimeter of the bottom panel is coupled to the first perimeter of the top panel. An internal wall is coupled between the top panel and the bottom panel to define a first chamber and a second chamber. The internal wall defines at least one passage therethrough that allows fluid communication between the first chamber and the second chamber. The first chamber and the second chamber are inflatable In various embodiments, a method of positioning a patient is disclosed. The method includes positioning a patient on an inflatable patient support. The inflatable patient support comprises a top panel defining a first perimeter, a bottom panel defining a second perimeter, and an internal wall. The second perimeter of the bottom panel is coupled to the first perimeter of the top panel and the internal wall is coupled between the top panel and the bottom panel to define a first chamber and a second chamber. The internal wall defines at least one passage therethrough that allows fluid communication between the first chamber and the second chamber. The first chamber and the second chamber are inflatable. An inflation device is coupled to the first chamber of the inflatable patient support and the first chamber of the inflatable patient support is inflated. The first chamber is inflated at a first rate by air flow from the inflation device The second chamber is inflated at a second rate by air flow from the first chamber through the at least one passage defined in the internal wall.

In various embodiments, an inflatable support is disclosed. The inflatable support includes a body having a top panel defining a first perimeter and a bottom panel defining a second perimeter. The second perimeter of the bottom panel is coupled to the first perimeter of the top panel. The body is configured to be inflated. The body defines a flat profile in a deflated configuration and a patient seating area in an inflated position. An internal wall is coupled between the top panel and the bottom panel. The internal wall, the top panel, and the bottom panel define a first chamber and a second chamber. The internal wall defines at least one passage therethrough configured to provide air flow between the first chamber and the second chamber. An inflation valve is coupled to the body and configured to be coupled to an inflation device. The inflation valve is configured to provide air flow from the inflation device to the first chamber such that a portion of the body defining the first chamber inflates at a first rate by air flow from the inflation device and a portion of the body defining the second chamber inflates at a second rate by air flow through the at least one passage.

BRIEF DESCRIPTION OF THE FIGURES

The features and advantages of the present invention will be more fully disclosed in, or rendered obvious by the following detailed description of the preferred embodiments, which are to be considered together with the accompanying drawings wherein like numbers refer to like parts and further wherein.

DETAILED DESCRIPTION

Figure 1:
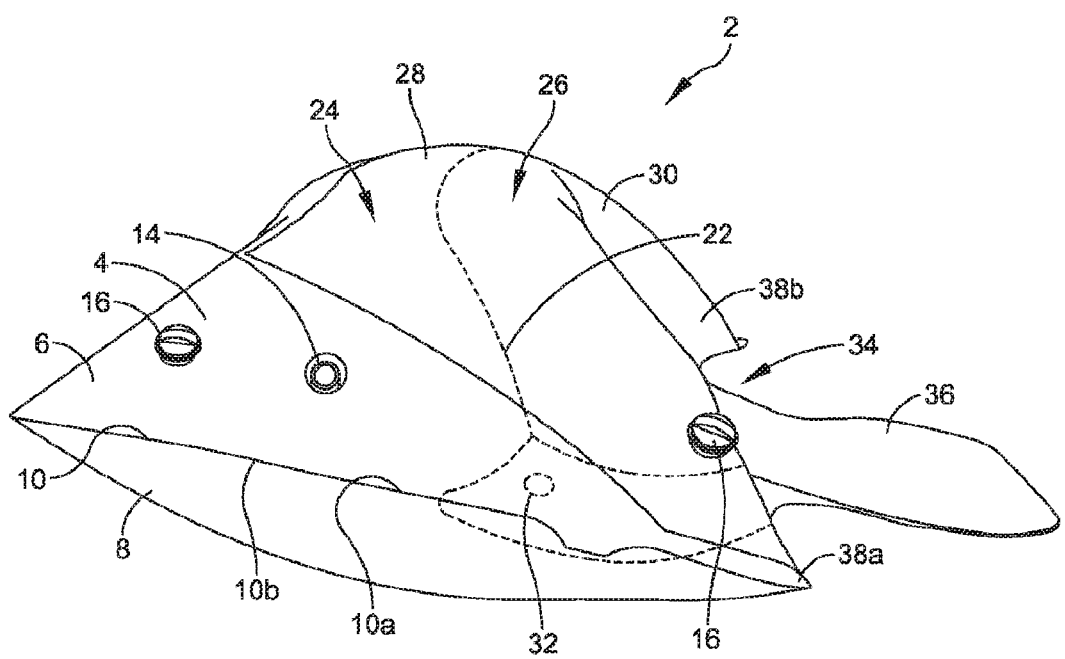
FIG. 1 illustrates a side view of an inflatable seat support in an inflated state, in accordance with some embodiments.

The description of the preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In this description, relative terms such as "horizontal," "vertical," "up," "down," "top," "bottom," as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal"

versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both moveable or rigid attachments or relationships, unless expressly described otherwise. The term "operatively coupled" is such an attachment, coupling, or connection that allows the pertinent structures to operate as intended by virtue of that relationship.

In various embodiments, an inflatable support is disclosed. The inflatable support includes a body having an upper panel and a lower panel. The upper panel and the lower panel have similar shapes and are coupled about a perimeter of each of the upper panel and the lower panel. At least one inner wall extends from an inner surface of the upper panel to an inner surface of the lower panel. The upper panel, the lower panel, and the inner wall define a first inflation chamber and a second inflation chamber. In some embodiments, a channel extends through the inner wall to couple the first and second inflation chambers. An inlet valve is coupled to a portion of the body and is configured to direct air flow into one of the first inflation chamber or the second inflation chamber.

FIGS. 1-5 illustrate an inflatable support 2, in accordance with some embodiments. The inflatable support 2 includes a body 4 defined by an upper panel 6 and a lower panel 8. A perimeter 10a of the upper panel 6 is coupled to a perimeter 10b of the lower panel 8 to define a perimeter 10 of the body 4. In some embodiments, the upper panel 6 and the lower panel 8 have a similar size and/or shape, although it will be appreciated that the upper panel 6 and the lower panel 8 can have a disparate size and/or shape in some embodiments. The upper panel 6 and/or the lower panel 8 can be a single panel or sheet of material and/or can include multiple sheets or material coupled together.

An internal wall 22 extends between and is coupled to an inner surface of the upper panel 6 and an inner surface of the lower panel 8. The internal wall 22 divides an inner volume of the body 4 into a first inflatable chamber 24 and a second inflatable chamber 26. The first and second inflatable chambers 24, 26 correspond to first and second inflatable portions 28, 30 of the body 4. For example, in the illustrated embodiment, the internal wall 22 defines a first, or rear, inflatable chamber 24 corresponding to a first, or rear, inflatable section 28 and the a second, or front, inflatable chamber 26 corresponding to a second, or front, inflatable section 30. Although a single internal wall 22 is illustrated, it will be appreciated that the inflatable support 2 can include a plurality of internal walls 22 defining two or more inflatable chambers corresponding to two or more inflatable portions of the body 4.

The inflatable support 2 includes one or more air inlets 14 formed in at least one of the upper panel 6 and/or the bottom panel 8. An inflation device, such as a blower (see FIG. 8) is coupled to one or more of the air inlets 14. Air is pumped from the inflation device into the internal volume of the body 4 to inflate the first inflatable section 28 and/or the second inflatable section 30. In some embodiments, the inflatable seat support 2 is configured for hands-free inflation. For example, in some embodiments, the air inlets 14 are configured to securely couple to a hose of the inflation device. Although embodiments are illustrated herein showing two air inlets 14, it will be appreciated that the inflatable support 2 can include a lesser and/or greater number of air inlets 14.

The air inlets 14 can include any suitable valve and/or port configured to allow air movement from the inflation device to at least one of the internal chambers 24, 26. For example, in some embodiments, the air inlets 14 include one-way valves configured to allow air movement from the inflation device to the internal chambers 24, 26 but prevent air movement out of the internal chambers 24, 26. In other embodiments, the air inlets 14 can include two-way valves/ports and a cap or other device configured to seal the air inlets 14 after inflation.

In some embodiments, the internal wall 22 defines one or more internal air passages 32 that allow fluid communication (e.g., air flow) between the first internal chamber 24 and the second internal chamber 26. During inflation of the body 4, the inflation device is coupled to one of the inlet ports 14 and an inflation gas, such as air, is pumped into one of the internal chambers 24, 26. For example, in the illustrated embodiment, the air inlets 14 provide fluid communication between an inflation device and the first internal chamber 24. The inflation gas flows through the air passage 32 from the first internal chamber 24 to the second internal chamber 26 and inflates the second inflatable portion 30. Although embodiments are illustrated having the inlet port 14 coupled to the first inflatable section 28, it will be appreciated that one or more inlet ports can be coupled to the second inflatable section 30 and/or any additional inflatable sections.

In some embodiments, the first inflatable portion 28 is configured to inflate at a first rate and the second inflatable portion 30 is configured to inflate at a second rate. For example, in the illustrated embodiment, the inlet port 14 is coupled to the first internal chamber 24. Air flow from the inflation device into the first internal chamber 24 inflates the first inflatable portion 28 at a first inflation rate. Simultaneously, air flows from the first internal chamber 24 to the second internal chamber 26 through the air passage(s) 32 defined in the internal wall 22. Air flow through the air passage(s) 32 into the second internal chamber 26 inflates the second inflatable portion 30 at a second inflation rate. In some embodiments, air flow through the air passage(s) 32 occurs after the first internal chamber 24 has been inflated to a predetermined pressure.

In some embodiments, the size ratio of the inlet ports 14 and/or the internal passage(s) 32 are configured to define an inflation ratio between the first inflation rate and the second inflation rate. The ratio between the first inflation rate and the second inflation ratio is selected to provide advantageous inflation of the inflatable support 2. For example, in some embodiments, the ratio between the first inflation rate and the second inflation rate is selected such that the first inflatable portion 28 inflates at a higher rate than the second inflatable portion 30. The ratio between the first inflation rate and the second inflation rate can be, for example, a 2:1 ratio, a 4:1 ratio, and/or any other suitable ratio. Although example inflation rates are given herein, it will be appreciated that the inflation ratio can be selected to provide any suitable ratio of inflation.

In some embodiments, the size of the inlet port(s) 14 and/or the internal air passage(s) 32 are configured to provide a predetermined inflation ratio. For example, in some embodiments, the inflation ratio between the first inflatable portion and the second inflatable portion is equal to X:1, where X is the area ratio between the inlet port(s) 14 and the internal air passage(s) 32. The area ratio can be calculated as:

$$\text{Area ratio} = \frac{A_L}{A_s * n}$$

where $A_L$ is equal to the area of the inlet port 14, $A_s$ is equal to the area of the internal passage(s) 32, and n is equal to the number of internal passage(s) 32 defined in the internal wall 22. As one example, the inflatable support can include a single inlet port 14 having a diameter of 0.7625" and two internal passage(s) 32 each heaving a diameter of about 0.375". In this example, the area ratio can be calculated as:

$$A_s = \pi \left(\frac{0.375}{2}\right)^2 = 0.1104466 \text{ in}^2$$

$$A_L = \pi \left(\frac{0.7625}{2}\right)^2 = 0.4566354 \text{ in}^2$$

$$\text{Area ratio} = \frac{A_L}{A_s * 2} = 2.0672222 \approx 2$$

In the example embodiments, the inflation ratio is equal to about 2:1 (e.g., the first inflatable portion 28 inflates at about twice the rate of the second inflatable portion 30). Although specific values are provided in this example, it will be recognized that the size of the inlet port(s) 14, the size of the internal passage(s) 32, and/or the number of inlet port(s) 14 and/or internal passage(s) 32 may be varied based on one or more parameters of the inflatable support 2.

In some embodiments, the inflation ratio between the first inflation rate and the second inflation rate is selected such that the first inflatable portion 28 substantially inflates prior to inflation of the second inflatable portion 30. For example, as discussed in more detail below, the first inflatable portion 28 may be substantially inflated prior to the second inflatable portion 30 to position a patient prior to inflation of the second inflatable portion 30. Inflation of the second inflatable portion 30 raises the patient into a seated position. Substantially inflating the first inflatable portion 28 prior to substantially inflating the second inflatable portion 30 causes a patient that is slightly off-center to be repositioned prior to raising the patient to a seated position, providing additional stability and preventing the patient from sliding off of the inflatable support 2 during inflation.

In some embodiments, one or more exhaust ports 16 are formed in at least one of the first inflatable portion 28 and/or the second inflatable portion 30 to allow deflation of the inflatable support 2. In the illustrated embodiment, the exhaust ports 16 are formed in the upper panel 6, although it will be appreciated that the exhaust ports 16 can additionally or alternatively be formed in the lower panel 8. The exhaust ports 16 can be sized and configured to provide deflation of the inflatable support 2 at a predetermined rate. In some embodiments, the exhaust port(s) 16 can have different sizes configured to provide different rates of deflation for each of the inflatable portions 28, 30 of the body 4.

In some embodiments, the inflatable seat support 2 comprises a bellows design sized and configured to support a patient during one or more procedures, such as, for example, a radiological imaging procedure. The shape of the upper panel 6 and the lower panel 8 are selected to provide a specific shape when inflated. For example, in some embodiments, the upper panel 6 and the lower panel 8 are selected such that a patient seating area 34 is defined by the inflatable support 2 in an inflated position (see FIG. 4). In some embodiments, the upper panel 6 and/or the lower panel 8 have a rounded profile in an inflated state configured to provide lateral stability to the inflatable support 2. Although embodiments are illustrated having a rounded profile, it will be appreciated that the upper panel 6 and/or the lower panel 8 can have any suitable profile shape, including but not limited to a squared profile, a rounded profile, an oblong profile, etc.

Figure 2:
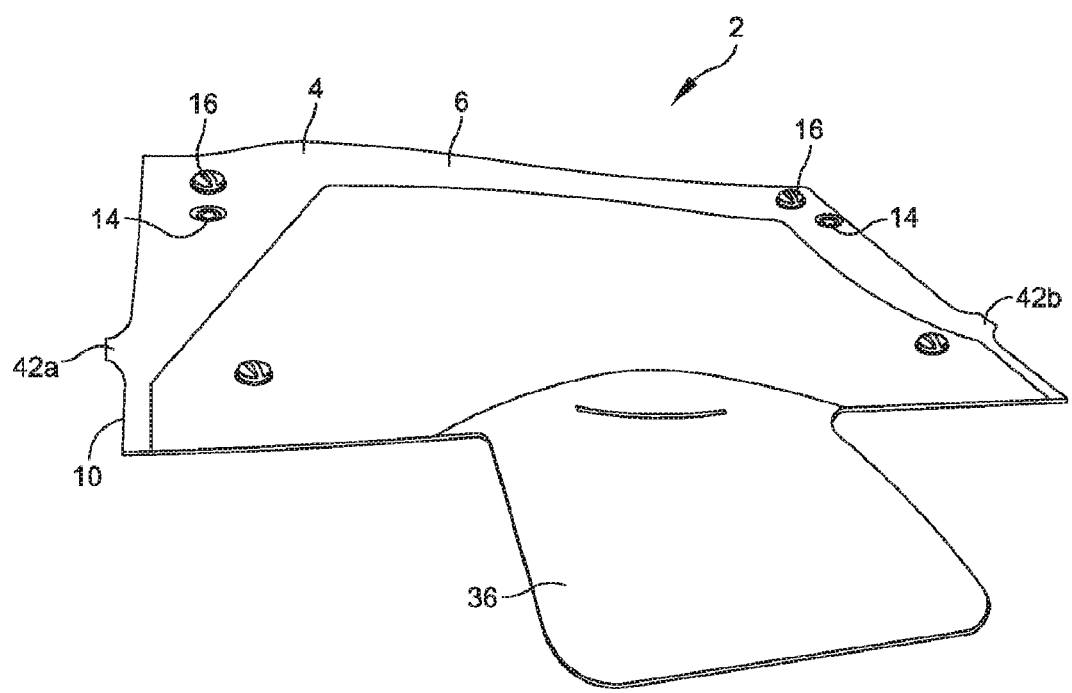
FIG. 2 illustrates a perspective view the inflatable seat support of FIG. 1 in a deflated state, in accordance with some embodiments.

In some embodiments, the patient seating area 34 is defined by the geometry of the second inflatable portion 30 when inflated and is not present (e.g., not defined) prior to inflation of the inflatable support 30 (see FIG. 2). The patient seating area 34 can be defined by the shape and perimeter 10 of a portion of the first and/or second inflatable portion 28, 30 when inflated. The first inflatable portion 28 is configured to position a patient within the patient seating area 34 prior to inflation of the second inflatable portion 30.

In some embodiments, a seating tongue 36 extends from body 4. The seating tongue 36 is positioned within the seating area 34 defined by the body 4. The seating tongue 36 is configured to be positioned beneath a patient to maintain 2 in a fixed positioned with respect to a patient during inflation, use, and deflation. In some embodiments, the seating tongue 36 includes a non-inflatable fabric strip that extends from the perimeter 10. When a patient is positioned on the seating tongue 36, the weight of the patient prevents the inflatable support 2 from moving with respect to the patient and/or a surface (such as a table). In some embodiments, the inflatable support 2 can be coupled to the surface by one or more additional means, such as straps, hook and loop connections, ties, and/or any other suitable attachment mechanism. The surface can be any suitable surface, including, but not limited to, a hospital bed or a radiological imaging table.

In some embodiments, the inflatable support 2 includes arm sections 38*a*, 38*b* extending from the body 4 and further defining the patient seating area 34. The arm sections 38*a*, 38*b* are configured to position a patient within the patient seating area 34 during inflation of the first inflatable portion 28. The arm sections 38*a*, 38*b* are defined by a portion of the first inflatable portion 28 and inflate at the first rate. As the arm sections 38*a*, 38*b* inflate, the patient is positioned in the center of the patient seating area 34. In some embodiments, the arm sections 38*a*, 38*b* provide stability to the patient and prevent the patient from sliding out of the patient seating area 34 during inflation of the inflatable support 2. Although embodiments are illustrated herein including two arm sections 38*a*, 38*b*, it will be appreciated that the inflatable support 2 can include a lesser or greater number of arm sections configured to position a patient within the patient seating area 34 during inflation.

In some embodiments, the body 4, the internal wall 22, and/or the tongue 36 include a radiolucent material. The radiolucent material allows x-rays and other radioscopic procedures to be performed on a patient supported by the inflatable support 2 without interfering with the imaging. The radiolucent material can be a flexible radiolucent plastic or other material, such as TPU, EVA, Nylon, PCV, and/or any other suitable material.

The internal wall 22 may be heat bonded, glued, ultrasonically bonded, and/or otherwise attached to the upper and lower panels 6, 8. In some embodiments, the location of the internal wall 22 determines the size and shape of the patient seating area 34, the support arms 38*a*, 38*b*, and/or one or more features of the inflatable support 2. In some embodiments, the inflatable support 2 is constructed without internal stringers or supports. Each of the internal chambers 24, 26 are defined by the inner surface of the body 4 and one or more internal chamber walls 22 that are coupled directly to the upper panel 6 and the lower panel 8 of the inflatable support 2. The internal chamber wall(s) 22 includes a radiolucent material. For example, in some embodiments, the internal chamber wall(s) 22 include the same radiolucent material as the body 4 of the inflatable support 2, although it will be appreciated that alternative and/or additional radiolucent materials can be used. By excluding internal supports, the inflatable support 2 advantageously allows imaging of a patient without interference due to stringers and/or other internal support members. The absence of internal stringers further allows the inflatable support 2 to lay flat in a deflated state. Although embodiments are illustrated herein without internal stringers/supports, it will be appreciated that the inflatable support 2 can include one or more internal stringers/supports in some embodiments.

In some embodiments, a strap 40 is coupled to the body 4 and/or the tongue 36. The strap 40 is configured to couple the inflatable support 2 to a patient. For example, in some embodiments, the strap 40 is coupled to the tongue 36. In other embodiments, the strap 40 is coupled to one or more portions of the body 4, such as, for example, protrusions 42a and 42b. The protrusions 42a, 42b comprise a non-inflatable section of the body 4. The strap 40 may be placed over a patient and buckled when the inflatable seat support 2 is in a deflated state. For example, the strap 40 may be placed over a patient's chest and/or abdomen. The strap 40 maintains the inflatable seat support 2 in contact with the patient in a deflated state and maintains the inflatable seat support 2 out of contact with imaging machinery, positioning machinery, and/or other medical machinery during positioning or movement of a patient. Although a single strap 40 is disclosed, those skilled in the art will recognize that the inflatable support 2 may comprise any suitable number of straps 40.

In operation, the inflatable support 2 is used to transition a patient from a first position, such as a laying position, to a second position, such as a seated position. The inflatable support 2 can be further configured to move the patient from the second position back to the first position. For example, in some embodiments, a patient is positioned on the inflatable support 2 when the inflatable support 2 is in a deflated state, such as shown in FIG. 2. An inflation device is coupled to one of the inlet ports 14. The inflatable support 2 is inflated to raise the patient from a laying position to a seated position for one or more procedures, such as, for example, radiological imaging. After the procedures are performed, one or more of the outlet ports 16 are unsealed to allow the first internal chamber 24 and the second internal chamber 26 to deflate, transitioning the patient from the second position back to the first position. In some embodiments, the inflatable support 2 may be inflated prior to the patient being seated on the inflatable support 2.

FIG. 2 illustrates one embodiment of the inflatable seat support 2 in a deflated state. As shown in FIG. 2, the inflatable seat support 2 defines a substantially rectangular shape in a deflated state. The upper panel 6 and the lower panel 8 lay flat in the deflated state. The patient seating area 36 (see, for example, FIGS. 3-4) is not visible in FIG. 2, as the patient seating area 36 is defined by the inflated geometry of the inflatable support 2. Similarly, the arm sections 40a, 40b are not shown and are only defined by the inflatable support 2 in an inflated state. By providing a rectangular, flat shape, the inflatable support 2 can be easily stored and/or positioned in the deflated state.

Figure 3:
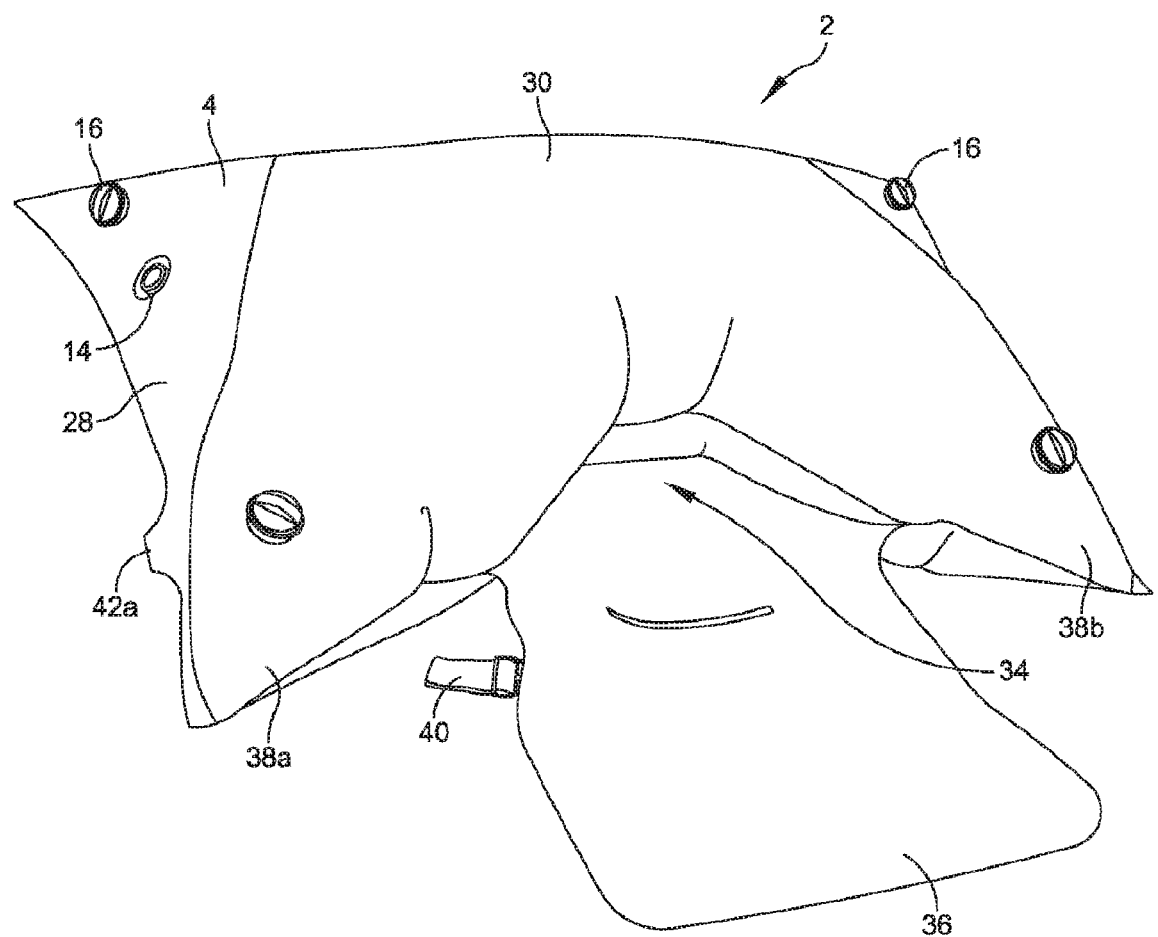
FIG. 3 illustrates a perspective view of the inflatable seat support of FIG. 1 in a partially inflated state, in accordance with some embodiments.
Figure 4:
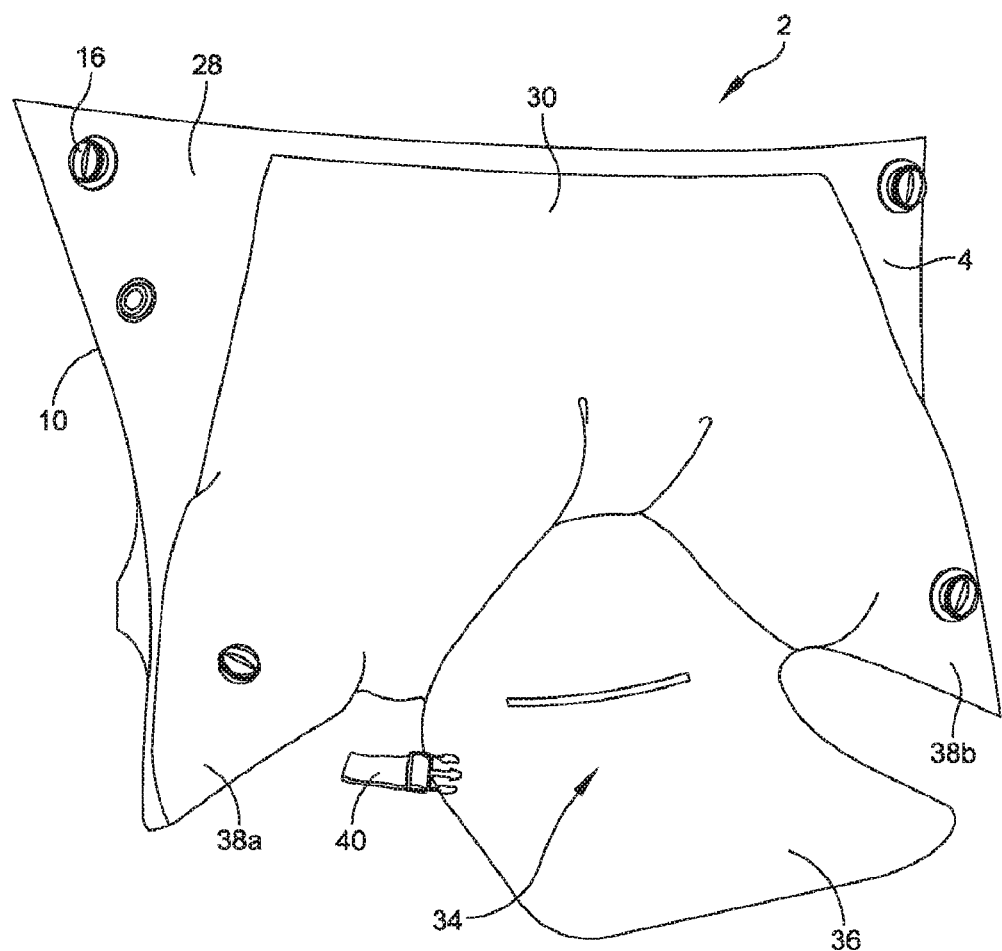
FIG. 4 illustrates a perspective view of the inflatable seat support of FIG. 1 in a fully inflated state, in accordance with some embodiments.
Figure 5:
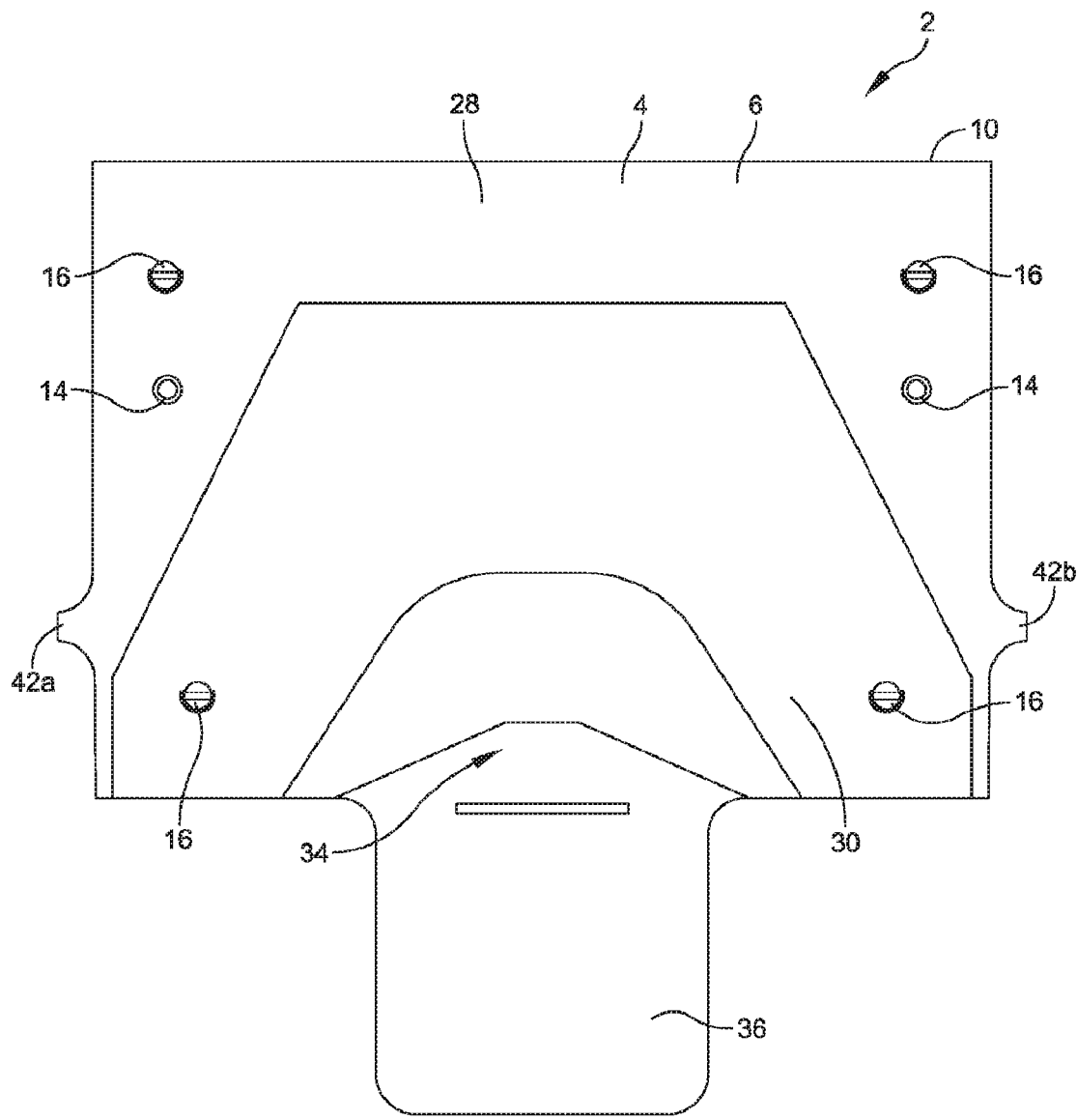
FIG. 5 illustrates a top down view of the inflatable seat support of FIG. 4, in accordance with some embodiments.

FIG. 3 illustrates the inflatable support 2 in a partially inflated state. The first inflatable portion 28 is partially inflated by, for example, an inflation device (not shown) coupled to one or more of the air inlet(s) 14. The first inflatable portion 28 is partially inflated. As the first inflatable portion 28 inflates, the air flow rate into the second inflatable portion 30 increases and the second inflatable portion 30 begins to inflate. The curved perimeter of the first inflatable portion 28 defines a patient seating area 34. The second inflatable portion 30 raises a patient from a flat, laying position (when the inflatable support 2 is deflated) into a sitting or partially-reclined position when the second inflatable portion 30 is at least partially inflated.

Figure 6:
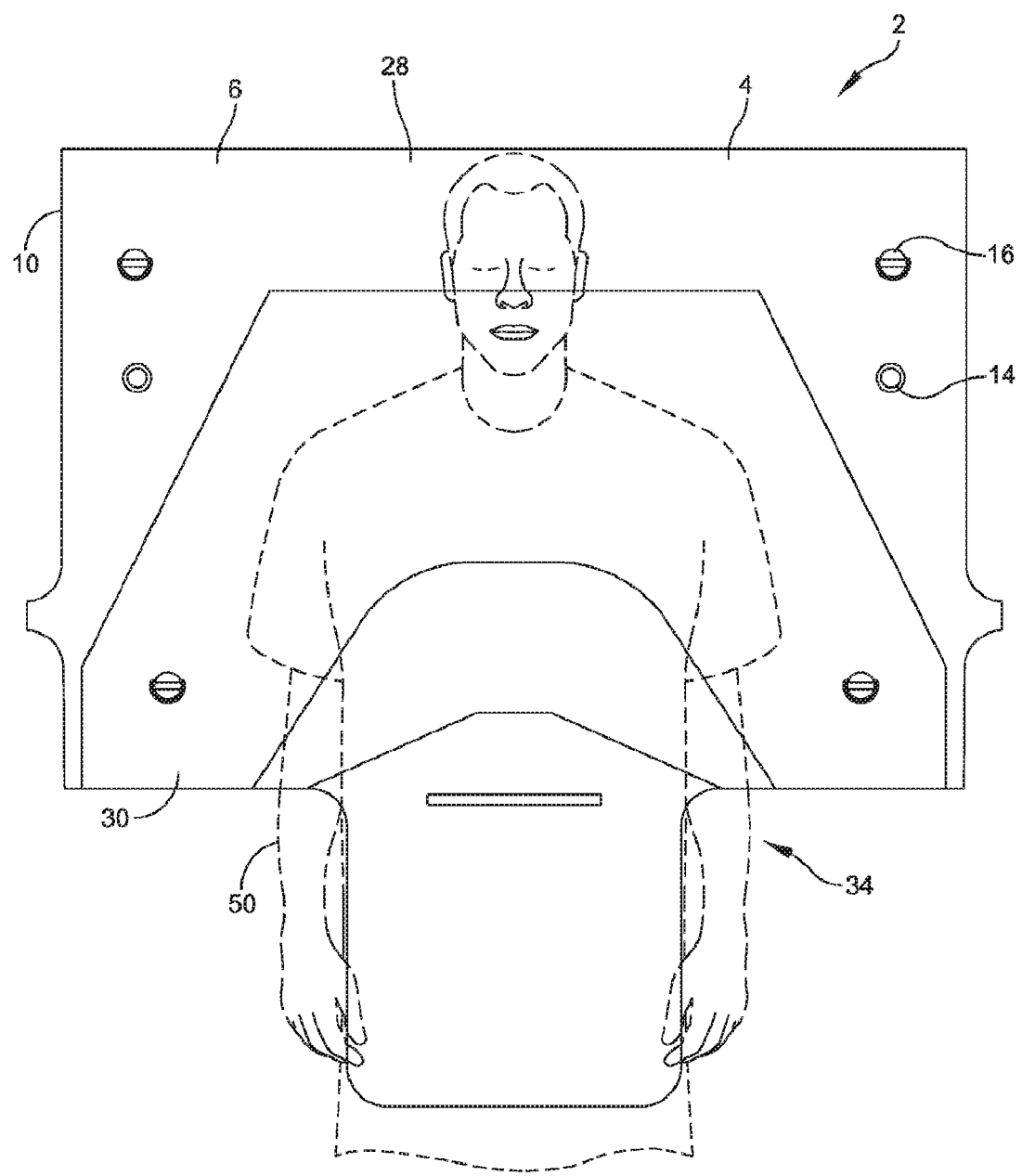
FIG. 6 illustrates a top down view of the inflatable support of FIG. 1 having a patient positioned in a patient seating area, in accordance with some embodiments.

FIG. 6 illustrates a top down view of one embodiment of the inflatable support 2 having a patient 50 positioned thereon. The patient 50 is positioned with an abdomen section located on the seating tongue 36 and the upper body extending onto the body 4 of the inflatable support 2. After the patient 50 is positioned, an inflation device is coupled to the air inlet 14 to inflate the first inflatable portion 28. The weight of the patient 50 on the seating tongue 36 maintains the position of the inflatable support 2 during inflation. As the first inflatable portion 28 inflates, the patient 50 is centered on the body 4 of the inflatable support 2. The second inflatable portion 30 is sequentially and/or simultaneously inflated to raise the patient 50 from a laying position to a seated position.

Although embodiments of the inflatable support 2 discussed herein include a first inflatable portion 28 and a second inflatable portion 30, it will be recognized that the inflatable support 2 may include any number of independent and/or interdependent inflatable sections defining one or more internal chambers. For example, in some embodiments, a second internal wall can define a third internal chamber corresponding to a third inflatable portion of an inflatable support 2. The third inflatable portion can be inflated at one of the first or second rates and/or can be inflated at a third rate, different from the first and second inflation rates. In some embodiments, one or more internal passages may be defined in the second internal wall to allow air to flow from the first and/or second internal chambers 24, 26 to the third internal chamber at a predetermined flow rate. In other embodiments, the second internal wall can define a third internal chamber separate and independently inflatable from the first and second internal chambers 24, 26 of the inflatable support 2.

Figure 7:
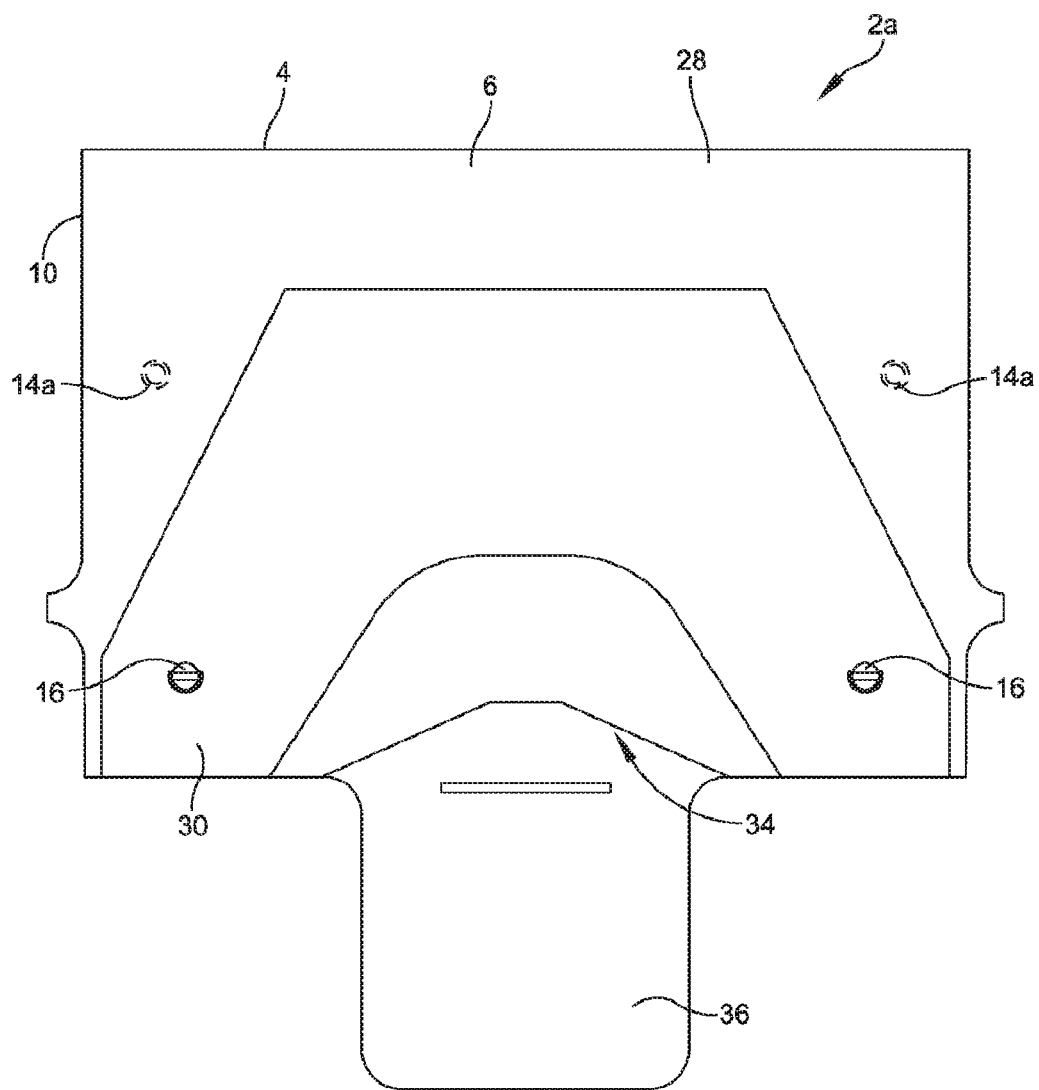
FIG. 7 illustrates a top-down view of an inflatable support having an inflation valve located on a bottom panel, in accordance with some embodiments.

FIG. 7 illustrates a top-down view of an inflatable support 2a having an air inlet located on a bottom panel, in accordance with some embodiments. The inflatable support 2a is similar to the inflatable support 2 discussed in conjunction with FIGS. 1-6, and similar description is not repeated herein. The inflatable support 2a includes at least one air inlet 14a (shown in phantom) formed through a bottom panel 8 of the inflatable support 2. The air inlet 14a allows an inflation device coupled to the air inlet 14a to be positioned away from a patient and/or connected to the inflatable support 2a while the patient is being positioned thereon without interfering with positioning the patient. The inflatable support 2a includes at least two deflation valves 16 coupled to an upper panel 6 of the body 4. In the illustrated embodiment, the deflation valves 16 are in fluid communication with the second internal chamber 26 such that opening the deflation valves 16 results in rapid deflation of the second inflatable portion 30 and slower deflation of the first inflatable portion 28, as air must travel from the first inflatable portion 28, through the internal passage(s) 32, and into the second inflatable portion 30 before being expelled through the deflation valves 16. In some embodiments, a patient's weight on the inflatable support 2a helps to force air from the first inflatable portion 28, into the second inflatable portion 30, and out of the deflation valves 16.

Figure 8:
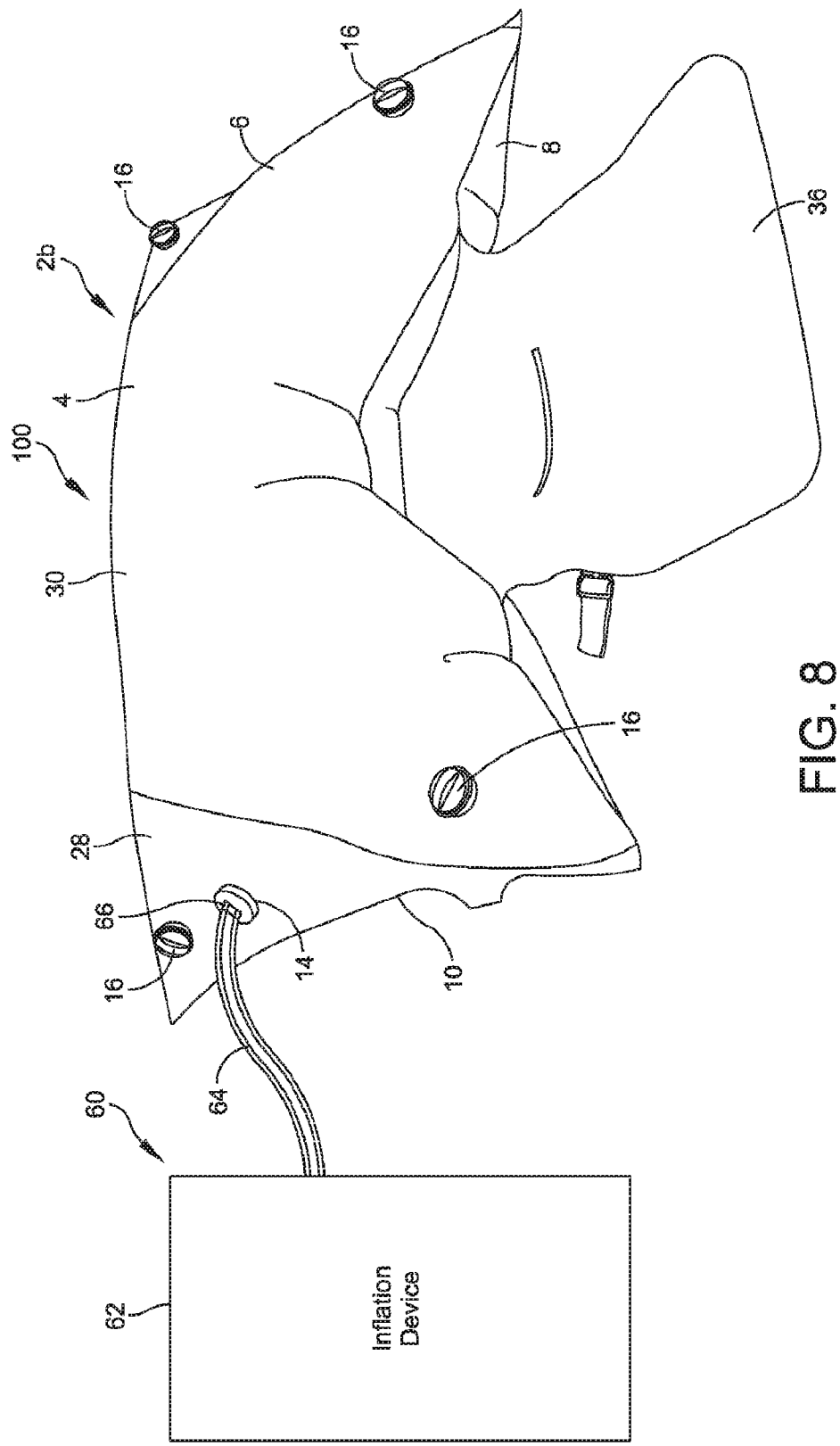
FIG. 8 illustrates a system including an inflatable support and an inflation device, in accordance with some embodiments.

FIG. 8 illustrates a system 100 including an inflatable support 2b coupled to an inflation device 60, in accordance with some embodiments. The inflatable support 2b is similar to the inflatable support 2 discussed above in conjunction with FIGS. 1-6, and similar description is not repeated herein. The inflation device 60 includes a pump 62 and a hose 64 coupling the pump 62 to one or more of the air inlet(s) 14 of the inflatable support 2b. The pump 62 is configured to provide positive air flow into the first internal chamber 24 of the inflatable support 2b. In some embodiments, the pump 62 is configured to provide a predetermined air flow rate. The predetermined air flow rate is selected to inflate the first inflatable portion 28 at a first inflation rate. In some embodiments, the hose 64 includes a coupling mechanism 66 configured to couple the hose 64 to the air inlet(s) 14. The coupling mechanism 66 can include any suitable coupling mechanism, such as a clamp, clip, thread, and/or any other suitable coupling mechanism.

Figure 9:
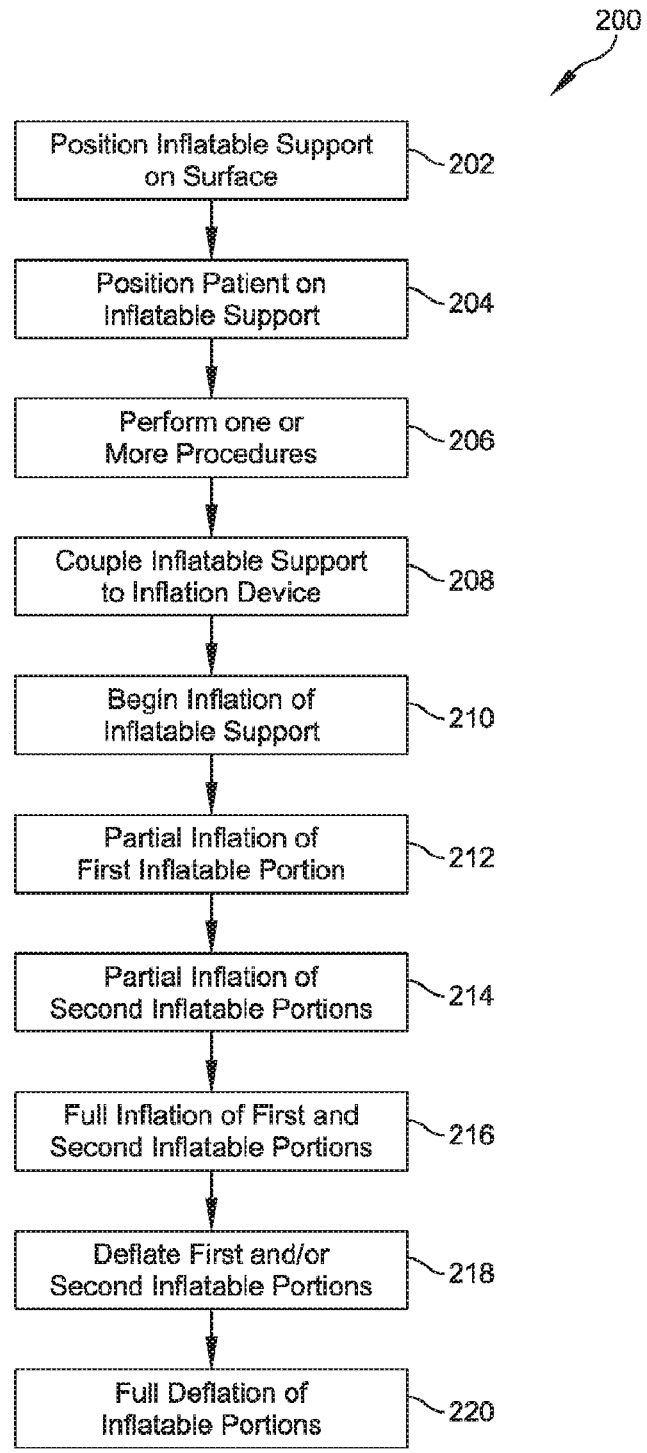
FIG. 9 illustrates a method of positioning a patient using an inflatable support, in accordance with some embodiments.

FIG. 9 is a flowchart illustrating a method 200 of positioning a patient for medical imaging using an inflatable support, in accordance with some embodiments. At step 202, an inflatable support, such as the inflatable support 2 discussed above, is positioned on a surface. The surface can include any suitable patient-receiving surface, such as an imaging table (e.g., radiological imaging table), a hospital bed, and/or any other suitable surface. At step 204, a patient is positioned over the inflatable support 2. The patient can be positioned such that the patient is seated on and/or otherwise applying weight to a tongue 36 extending from a body 4 of the inflatable support 2. At step 206, one or more imaging and/or other medical procedures are performed.

At step 208, an inflation device, such as inflation device 60, is coupled to at least one of the air inlets 14 on the body 4. The inflation device 60 can include a hose 64 coupled to the air inlets 14 by one or more coupling mechanisms 66 and/or can be manually coupled by a user.

At step 210, the inflation device begins inflating the inflatable support 2 through the air inlet(s) 14. The inflation device provides a positive air flow into the first internal chamber 24 of the inflatable support 2. At step 212, the first inflatable portion 28 is partially inflated by the positive air flow and positions the patient within a seating area 34. The first inflatable portion 28 is inflated at a first rate by the positive air flow from the inflation device. As the first inflatable portion 28 inflates, the patient is centered with respect to the inflatable support 2 and positioned within the seating area 34.

At step 214, the second inflatable portion 30 beings to inflate. The second inflatable portion 30 is inflated by a positive air flow from the first internal chamber 24 into the second internal chamber 26 through one or more internal passages 32 defined in an internal wall 22. The second inflatable portion 30 is inflated at a second flow rate. In some embodiments, the second flow rate is determined by the ratio between the air inlet(s) 14 and the internal passage(s) 32 as discussed above. The second inflation rate is less than the first inflation rate.

At step 216, the first inflatable portion 28 and the second inflatable portion 30 fully inflate and position the patient in a seated position. In some embodiments, the first inflatable portion 28 includes one or more arm sections 38a, 38b configured to maintain the patient in the center of the patient seating area 34 during inflation of the second inflatable portion 30.

At step 218, at least one deflation valve 16 is opened to allow air to flow out of the first and second internal chambers 24, 26. In some embodiments, the one or more deflation valves are sized and configured to provide deflation of the first and second inflatable portions 28, 30 at a predetermined rate of deflation. For example, in some embodiments, one or more deflation valves 16 are coupled to the second inflatable portion 30 and provide deflation of the second inflatable portion 30 at a first rate. The one or more deflation valves 16 also provide deflation of the first inflatable portion 28 at a second deflation rate which is less than the first deflation rate. In other embodiments, at least one deflation valve 16 is coupled to the first inflatable portion 28 and at least one deflation valve 16 is coupled to the second inflatable portion 30.

At step 220, the inflatable support 2 is fully deflated and the patient is returned to a laying position. The patient can be subsequently removed from the inflatable support 2 and/or remain on the inflatable support 2 to allow the patient to be transitioned back to the seated position for subsequent and/or additional procedures.

Although the subject matter has been described in terms of exemplary embodiments, it is not limited thereto. Rather, the appended claims should be construed broadly, to include other variants and embodiments, which may be made by those skilled in the art.

What is claimed is:

1. An inflatable patient support, comprising:
   a top panel defining a first perimeter;
   a bottom panel defining a second perimeter, wherein the second perimeter of the bottom panel is coupled to the first perimeter of the top panel, wherein the top panel and the bottom panel define a substantially rectangular outer perimeter in a deflated state, wherein the top panel and the bottom panel define a first arm section and a second arm section in an inflated state, the top panel and the bottom panel define a substantially flat profile in a deflated state and a rounded profile configured to provide lateral stability in the inflated state; and
   an internal wall coupled between the top panel and the bottom panel to define a first chamber and a second chamber, wherein the internal wall defines at least one passage therethrough, wherein the at least one passage allows fluid communication between the first chamber and the second chamber, wherein the first chamber and the second chamber are inflatable, wherein the first chamber is configured to be inflated at a first inflation rate and the second inflation chamber is configured to be inflated at a second inflation rate such that the first chamber is substantially inflated prior to inflation of the second chamber, wherein the first chamber includes the first arm section and the second arm section, and wherein the first arm section and the second arm section are configured to position a patient in the center of a patient seating area defined between the first arm section and the second arm section when the first arm section and the second arm section are inflated, and wherein the patient seating area is defined by a shape and perimeter of a portion of the top panel and the bottom panel only in the inflated state.

2. The inflatable patient support of claim 1, comprising an inlet valve formed on at least one of the top panel or the bottom panel, wherein the inlet valve is coupled to the first chamber, wherein the inlet valve is configured to couple an inflation device to the first chamber.

3. The inflatable patient support of claim 2, wherein the first chamber is inflated at the first inflation rate by air flow from the inlet valve and the second chamber is inflated at the second inflation rate by air flow through the at least one passage.

4. The inflatable patient support of claim 3, wherein the second inflation rate is equal to a ratio between an area of the inlet valve and an area of the at least one passage.

5. The inflatable patient support of claim 3, wherein the first rate is about twice the second rate.

6. The inflatable patient support of claim 1, wherein the top panel, the bottom panel, and the internal wall each comprise a radiolucent material.

7. The inflatable patient support of claim 1, comprising an outlet valve formed on at least one of the top panel or the bottom panel.

8. The inflatable patient support of claim 1, comprising a seating tongue extending from at least one of the first perimeter or the second perimeter, wherein the seating tongue is sized and configured to receive a user.

9. The inflatable patient support of claim 1, comprising at least one strap coupled to one of the first perimeter or the second perimeter, wherein the at least on strap is configured to couple a user to the inflatable patient support.

10. The inflatable patient support of claim 1, wherein the top panel and the bottom panel define one or more protrusions when the inflatable patient support is inflated, and wherein the protrusions are configured to maintain a patient in a fixed position during inflation.

11. The inflatable patient support of claim 1, wherein each of the top panel, the bottom panel, and the internal wall comprise a radiolucent material.

12. A method of positioning a patient, comprising:
positioning a patient on an inflatable patient support, wherein the inflatable patient support comprises a top panel defining a first perimeter, a bottom panel defining a second perimeter, and an internal wall, wherein the top panel and the bottom panel define a substantially rectangular outer perimeter in a deflated state, wherein the top panel and the bottom panel define a first arm section and a second arm section in an inflated state, wherein the second perimeter of the bottom panel is coupled to the first perimeter of the top panel, wherein the internal wall is coupled between the top panel and the bottom panel to define a first chamber and a second chamber, wherein the internal wall defines at least one passage therethrough, wherein the at least one passage allows fluid communication between the first chamber and the second chamber, wherein the first chamber and the second chamber are inflatable, and wherein the top panel and the bottom panel define a substantially flat profile in a deflated state and a rounded profile configured to provide lateral stability in the inflated state;
coupling an inflation device to the first chamber of the inflatable patient support; providing air flow from the inflation device to the inflatable patient support, wherein the first chamber of the inflatable patient support is inflated at a first rate by air flow from the inflation device and the second chamber is inflated at a second rate by air flow from the first chamber through the at least one passage defined in the internal wall, wherein the first chamber is substantially inflated prior to inflation of the second chamber, wherein the first chamber includes the first arm section and the second arm section, and wherein the first arm section and the second arm section are configured to position a patient in the center of a patient seating area defined between the first arm section and the second arm section when the first arm section and the second arm section are inflated, and wherein the patient seating area is defined by a shape and perimeter of a portion of the top panel and the bottom panel only in the inflated state.

13. The method of claim 12, wherein positioning the patient on the inflatable patient support comprises positioning the patient on a tongue extending from one of the first perimeter or the second perimeter.

14. The method of claim 13, wherein prior to positioning the patient on the inflatable patient support, the method comprises positioning the patient support on an imaging table.

15. The method of claim 12, wherein coupling the inflation device to the first chamber comprises coupling the inflation device to an inlet valve formed in one of the top panel or the bottom panel, wherein the inlet valve provides fluid communication between the inflation device and the first chamber.

16. The method of claim 15, wherein the inlet valve is configured to provide one-way air flow from the inflation device to the first chamber.

17. The method of claim 12, comprising performing one or more imaging operations on the patient prior to inflation of the inflatable patient support.

18. The method of claim 12, comprising deflating the inflatable patient support using one or more deflation valves coupled to at least one of the top panel or the bottom panel.

19. The method of claim 18, wherein the deflation valve extends though the at least one of the top panel or the bottom panel to the second chamber.

20. An inflatable support, comprising:
a body comprising a top panel defining a first perimeter and a bottom panel defining a second perimeter, wherein the second perimeter of the bottom panel is coupled to the first perimeter of the top panel, wherein the body is configured to be inflated, wherein the body defines a flat profile in a deflated configuration and a patient seating area in an inflated position, wherein the patient seating area is defined by a first arm section and a second arm section defined only in the inflated configuration, wherein the top panel and the bottom panel define a substantially rectangular outer perimeter in a deflated state, and the top panel and the bottom panel define a substantially flat profile in a deflated state and a rounded profile configured to provide lateral stability in the inflated state;
an internal wall coupled between the top panel and the bottom panel, wherein the internal wall, the top panel, and the bottom panel define a first chamber and a second chamber, wherein the internal wall defines at least one passage therethrough configured to provide air flow between the first chamber and the second chamber, and wherein each of the top panel, the bottom panel, and the internal wall comprise a radiolucent material; and
an inflation valve coupled to the body and configured to be coupled to an inflation device, wherein the inflation valve is configured to provide air flow from the inflation device to the first chamber such that a portion of the body defining the first chamber inflates at a first rate by air flow from the inflation device and a portion of the body defining the second chamber inflates at a second rate by air flow through the at least one passage, and wherein the first chamber is substantially inflated prior to inflation of the second chamber, wherein the first chamber includes the first arm section and the second arm section, and wherein the first arm section and the second arm section are configured to position a patient in the center of the patient seating area defined between the first arm section and the second arm section when the first arm section and the second arm section are inflated, and wherein the patient seating area is defined by a shape and perimeter of a portion of the top panel and the bottom panel only in the inflated state.

\* \* \* \* \*